United States Patent
Adeyanju et al.

(10) Patent No.: US 12,006,511 B2
(45) Date of Patent: Jun. 11, 2024

(54) RECOMBINANT PD-L1 PEPTIDES AND METHODS OF USE

(71) Applicants: The Medical College of Wisconsin, Inc., Milwaukee, WI (US); University of Virginia Patent Foundation, Charlottesville, VA (US)

(72) Inventors: Kaothara Oluwakemi Adeyanju, Milwaukee, WI (US); Jeffrey A. Medin, Shorewood, WI (US); Robert Blake Hill, Milwaukee, WI (US); Lawrence G. Lum, Charlottesvilla, VA (US)

(73) Assignees: The Medical College of Wisconsin, Inc., Milwaukee, WI (US); University of Virginia Patent Foundation, Charlottesville, VA (US)

( * ) Notice: Subject to any disclaimer, the term of this patent is extended or adjusted under 35 U.S.C. 154(b) by 9 days.

(21) Appl. No.: 17/046,287

(22) PCT Filed: Apr. 14, 2020

(86) PCT No.: PCT/US2020/028145
§ 371 (c)(1),
(2) Date: Oct. 8, 2020

(87) PCT Pub. No.: WO2020/214606
PCT Pub. Date: Oct. 22, 2020

(65) Prior Publication Data
US 2023/0135850 A1    May 4, 2023

Related U.S. Application Data

(60) Provisional application No. 62/834,242, filed on Apr. 15, 2019.

(51) Int. Cl.
C12N 15/79 (2006.01)
C07K 14/705 (2006.01)
C12N 5/0783 (2010.01)

(52) U.S. Cl.
CPC ...... *C12N 5/0636* (2013.01); *C07K 14/70532* (2013.01); *C12N 2501/2302* (2013.01); *C12N 2501/24* (2013.01); *C12N 2501/48* (2013.01); *C12N 2501/51* (2013.01); *C12N 2501/515* (2013.01)

(58) Field of Classification Search
CPC ......... C12N 5/0636; C12N 2310/3513; C12N 15/79; C12N 15/85; C12N 15/86; C12N 2510/00; C07K 14/70532; C07H 21/04
See application file for complete search history.

(56) References Cited

U.S. PATENT DOCUMENTS 7,371,826 B2    5/2008  Presta
2018/0291343 A1  10/2018  Duchateau et al.

FOREIGN PATENT DOCUMENTS

WO      2017072539 A1    5/2017

OTHER PUBLICATIONS

Namdev et al., 2016 (Research J. Pharm. and Tech., 9(3), p. 305-312).*
Rehman et al., 2016 (Current Drug targets, vol. 17, p. 1172-1188).*
Mun et al., 2022 (Journal of Controlled Release, vol. 350, p. 716-733).*
Bryan et al., 2013 (http://www.elsevierblogs.com/currentcomments/?p=962, Implications of protein fold switching, p. 1-4).*
Maqbool et al., 2015 (Biochemical Society Transactions, vol. 43, No. 5, p. 1011-1017).*
Cruz et al., 2017 (Methods in Molecular Biology, vol. 1654, Chapter 5, pp. 55-75).*
Altschul et al., Gapped BLAST and PSI-BLAST: A New Generation of Protein Database Search Programs, Nucleic Acids Research, 1997, 25(17):3389-3402.
Bluestone et al., Type 1 Diabetes Immunotherapy using Polyclonal Regulatory T Cells, Science Translational Medicine, 2015, 7(315):315ra189, pp. 1-34.
Gong et al., Secreted PD-L1 Variants Mediate Resistance to PD-L1 Blockade Therapy in Non-Small Cell Lung Cancer, Journal of Experimental Medicine, 2019, 216(4):982-1000.
Invitrogen™ By Life Technologies, pcDNA™ 3.4 Topo™ TA Cloning Kit: Five-Minute Cloning and Expression of Taq Polymerase-Amplified PCR Products in Mammalian Cells, Catalog No. A14697, 2013, 29 pages.
Karlin et al., Methods for Assessing the Statistical Significance of Molecular Sequence Features by Using General Scoring Schemes, Proceedings of the National Academy of Sciences, 1990, 87(6):2264-2268.
Mahoney et al., A Secreted PD-L1 Splice Variant that Covalently Dimerizes and Mediates Immunosuppression, Cancer Immunology, Immunotherapy, 2019, 68:421-432.
Sharp et al., The Codon Adaptation Index—A Measure of Directional Synonymous Codon Usage Bias, and its Potential Application, Nucleic Acids Research, 1987, 15(3):1281-1295.
Stathopoulou et al., PD-1 Inhibitory Receptor Downregulates Asparaginyl Endopeptidase and Maintains Foxp3 Transcription Factor Stability in Induced Regulatory T Cells, Immunity, 2018, 49(2):247-263.
PCT International Search Report and Written Opinion, PCT/US2020/028145, dated Aug. 4, 2020, 9 pages.

* cited by examiner

*Primary Examiner* — Shin Lin Chen
(74) *Attorney, Agent, or Firm* — Quarles & Brady LLP (57) ABSTRACT

The present disclosure provides soluble truncated mutant programmed death-ligand 1 (PD-L1) peptides. Polynucleotides and vectors encoding the soluble truncated mutant PD-L1 peptides are also provided. Further, methods of using the soluble truncated mutant peptides to promote differentiation of CD4+ effector T (Th1) cells into Foxp3+ regulatory T (Treg) cells are provided.

15 Claims, 6 Drawing Sheets
Specification includes a Sequence Listing.

FIG. 1A

PDL1WT peptide (SEQ ID NO: 1)
AFTVTVPKD̲LYVVEYGSNMTIECKFPVEKQLDLAALIVYY̲WEMEDKNIIQFV̲HGEEDLKVQHSSYRQRARLLKDQLSLGN
AALQITDVKLQDAGVYRCMIS̲YGGAD̲Y̲K̲R̲ITVKVNAPY

PDL1A peptide with Y123W mutation (SEQ ID NO: 2)
AFTVTVPKDLYVVEYGSNMTIECKFPVEKQLDLAALIVYVWEMEDKNIIQFVHGEEDLKVQHSSYRQRARLLKDQLSLGN
AALQITDVKLQDAGVYRCMISYGGADW̲KRITVKVNAPY

PDL1C peptide with Y56I, V68I, S117I and Y123W mutations (SEQ ID NO: 3)
AFTVTVPKDLYVVEYGSNMTIECKFPVEKQLDLAALIVI̲WEMEDKNIIQFI̲HGEEDLKVQHSSYRQRARLLKDQLSLGNA
ALQITDVKLQDAGVYRCMII̲YGGADW̲KRITVKVNAPY

PDL1D peptide with D26E, Y56I, V68I, S117I, D122E, Y123W and R125M mutations (SEQ ID NO: 4)
AFTVTVPKE̲LYVVEYGSNMTIECKFPVEKQLDLAALIVI̲WEMEDKNIIQFI̲HGEEDLKVQHSSYRQRARLLKDQLSLGNA
ALQITDVKLQDAGVYRCMII̲YGGAE̲W̲K̲M̲ITVKVNAPY

FIG. 1B

PDL1A vector insert (SEQ ID NO: 5)
GCCACCATGGACTGGACTTGGAGAATCCTGTTTCTGGTAGCTGCAACTGGAGCTCACTCTGCCTTCACCGTGACCGTGCCAAGG
ACCTGTACGTGGTGGAGTACGGCAGCAACATGACCATCGAGTGCAAGTTCCCCGTGGAGAAGCAGCTGGACCTGGCCGCCCTGATCG
TGTACTGGGAGATGGAGGACAAGAACATCATCCAGTTCGTGCACGGCGAGGAGGACCTGAAGGTGCAGCACAGCAGCTACCGGCA
GCGGGCCCGGCTGCTGAAGGACCAGCTGAGCCTGGGCAACGCCGCCCTGCAGATCACCGATGTGAAGCTGCAGGACGCCGGCGTG
TACCGGTGCATGATCAGCTACGGCGGAGGCCCTGACTACCAAGCGCATCATCACCATCAAGCAGCTGGAGAGCGGCGGAGGCTCAGGAGAG
GCGGAGGCGGCTCAGGAAACGACATCTTCGAGGCCCAGAAGATCGAGTGGCACGAGCATCATCACCATCACCACTAG

PDL1C vector insert (SEQ ID NO: 6)
GCCACCATGGACTGGACTTGGAGAATCCTGTTTCTGGTAGCTGCAACTGGAGCTCACTCTGCCTTCACCGTGACCGTGCCAAGG
ACCTGTACGTGGTGGAGTACGGCAGCAACATGACCATCGAGTGCAAGTTCCCCGTGGAGAAGCAGCTGGACCTGGCCGCCCTGATCG
TGATCTGGGAGATGGAGGACAAGAACATCATCCAGTTCATCCACGGCGAGGAGGACCTGAAGGTGCAGCACAGCAGCTACCGGCAG
CGGGCCCGGCTGCTGAAGGACCAGCTGAGCCTGGGCAACGCCGCCCTGCAGATCACCGATGTGAAGCTGCAGGACGCCGGCGTGT
ACCGGTGCATGATCAGCTACGGCGGAGGCCCTGACTACAAGCGCATCATCACCATCAAGCAGCTGGAGAGCGGCGGAGGCTCAGGAGG
CGGAGGCGGCTCAGGAAACGACATCTTCGAGGCCCAGAAGATCGAGTGGCACGAGCATCATCACCATCACCACTAG

PDL1D vector insert (SEQ ID NO: 7)
GCCACCATGGACTGGACTTGGAGAATCCTGTTTCTGGTAGCTGCAACTGGAGCTCACTCTGCCTTCACCGTGACCGTGCCAAGG
AGCTGTACGTGGTGGAGTACGGCAGCAACATGACCATCGAGTGCAAGTTCCCCGTGGAGAAGCAGCTGGACCTGGCCGCCCTGATC
GTGATCTGGGAGATGGAGGACAAGAACATCATCCAGTTCATCCACGGCGAGGAGGACCTGAAGGTGCAGCACAGCAGCTACCGGCA
GCGGGCCCGGCTGCTGAAGGACCAGCTGAGCCTGGGCAACGCCGCCCTGCAGATCACCGATGTGAAGCTGCAGGACGCCGGCGTG
TACCGGTGCATGATCAGCTACGGCGGAGTCATCTACGGCGGAGTGGAAGATGATGAGCGCCTGAAGCGTGAAGCGCCCTGAAGGTGAACGCCTGGCTGGTGCATCATCACCATCACCACTAG
CGGAGGCGGCTCAGGAGACATTTGAGGCCCAGAAGATCGAGTGGCACGAGCATCATCACCATCACCACTAG

KEY:
Kozak sequence | Start codon | tPA Signal Sequence | PDL1A | Polyglycine linker | AviTag | 6X His tag | Stop codon

FIG. 3

T cell analysis: % cell viability

| | Sample | Live cells | Live CD4+ |
|---|---|---|---|
| No PDL1 treatment (Control samples) | 1: Foxp3+ isotype_024.fcs | 88.7 | 35.7 |
| | 2: Tbet+ isotype_023.fcs | 88.7 | 35.5 |
| | 3: 1uM Rapamycin_021.fcs | 69.6 | 18.9 |
| | 4: TGFbeta_020.fcs | 88.5 | 37.3 |
| | 5: 1uM Tem_022.fcs | 86.8 | 36.2 |
| PDL1A beads | 6: PDL1A_A1_1_011.fcs | 33.7 | 59.5 |
| | 7: PDL1A_A3_1_012.fcs | 21.1 | 53.5 |
| | 8: PDL1A_A5_1_013.fcs | 36.9 | 56.8 |
| PDL1C beads | 9: PDL1C_C1_1_014.fcs | 28.5 | 58.9 |
| | 10: PDL1C_C3_1_015.fcs | 26.6 | 54.8 |
| | 11: PDL1C_C5_1_016.fcs | 27.8 | 57 |
| PDL1D beads | 12: PDL1D_D1_1_017.fcs | 23.3 | 57.3 |
| | 13: PDL1D_D3_1_018.fcs | 36.4 | 57.8 |
| | 14: PDL1D_D5_1_019.fcs | 36.1 | 52.9 |
| PDL1 WT beads | 15: WT_WT 1_1_008.fcs | 37.6 | 58.3 |
| | 16: WT_WT 3_1_009.fcs | 39.6 | 56.8 |
| | 17: WT_WT 5_1_010.fcs | 39.4 | 55.5 |

PDL1 Tx
bead: cell
1_1 = 1:1
3_1 = 3:1
5_1 = 5:1

FIG. 5

SEQUENCE LISTING

```
<160> NUMBER OF SEQ ID NOS: 7

<210> SEQ ID NO 1
<211> LENGTH: 117
<212> TYPE: PRT
<213> ORGANISM: Artificial Sequence
<220> FEATURE:
<223> OTHER INFORMATION: Synthetic - PDL1WT peptide

<400> SEQUENCE: 1

Ala Phe Thr Val Thr Val Pro Lys Asp Leu Tyr Val Val Glu Tyr Gly
1               5                   10                  15

Ser Asn Met Thr Ile Glu Cys Lys Phe Pro Val Glu Lys Gln Leu Asp
            20                  25                  30

Leu Ala Ala Leu Ile Val Tyr Trp Glu Met Glu Asp Lys Asn Ile Ile
        35                  40                  45

Gln Phe Val His Gly Glu Glu Asp Leu Lys Val Gln His Ser Ser Tyr
    50                  55                  60

Arg Gln Arg Ala Arg Leu Leu Lys Asp Gln Leu Ser Leu Gly Asn Ala
65                  70                  75                  80

Ala Leu Gln Ile Thr Asp Val Lys Leu Gln Asp Ala Gly Val Tyr Arg
                85                  90                  95
```

Cys Met Ile Ser Tyr Gly Gly Ala Asp Tyr Lys Arg Ile Thr Val Lys
                100                 105                 110

Val Asn Ala Pro Tyr
        115

<210> SEQ ID NO 2
<211> LENGTH: 117
<212> TYPE: PRT
<213> ORGANISM: Artificial Sequence
<220> FEATURE:
<223> OTHER INFORMATION: Synthetic- PDL1A (Y123W) peptide

<400> SEQUENCE: 2

Ala Phe Thr Val Thr Val Pro Lys Asp Leu Tyr Val Val Glu Tyr Gly
1               5                   10                  15

Ser Asn Met Thr Ile Glu Cys Lys Phe Pro Val Glu Lys Gln Leu Asp
            20                  25                  30

Leu Ala Ala Leu Ile Val Tyr Trp Glu Met Glu Asp Lys Asn Ile Ile
        35                  40                  45

Gln Phe Val His Gly Glu Glu Asp Leu Lys Val Gln His Ser Ser Tyr
    50                  55                  60

Arg Gln Arg Ala Arg Leu Leu Lys Asp Gln Leu Ser Leu Gly Asn Ala
65                  70                  75                  80

Ala Leu Gln Ile Thr Asp Val Lys Leu Gln Asp Ala Gly Val Tyr Arg
                85                  90                  95

Cys Met Ile Ser Tyr Gly Gly Ala Asp Trp Lys Arg Ile Thr Val Lys
                100                 105                 110

Val Asn Ala Pro Tyr
        115

<210> SEQ ID NO 3
<211> LENGTH: 117
<212> TYPE: PRT
<213> ORGANISM: Artificial Sequence
<220> FEATURE:
<223> OTHER INFORMATION: Synthetic- PDL1C (Y56I, V68I, S117I and Y123W)
      peptide

<400> SEQUENCE: 3

Ala Phe Thr Val Thr Val Pro Lys Asp Leu Tyr Val Val Glu Tyr Gly
1               5                   10                  15

Ser Asn Met Thr Ile Glu Cys Lys Phe Pro Val Glu Lys Gln Leu Asp
            20                  25                  30

Leu Ala Ala Leu Ile Val Ile Trp Glu Met Glu Asp Lys Asn Ile Ile
        35                  40                  45

Gln Phe Ile His Gly Glu Glu Asp Leu Lys Val Gln His Ser Ser Tyr
    50                  55                  60

Arg Gln Arg Ala Arg Leu Leu Lys Asp Gln Leu Ser Leu Gly Asn Ala
65                  70                  75                  80

Ala Leu Gln Ile Thr Asp Val Lys Leu Gln Asp Ala Gly Val Tyr Arg
                85                  90                  95

Cys Met Ile Ile Tyr Gly Gly Ala Asp Trp Lys Arg Ile Thr Val Lys
                100                 105                 110

Val Asn Ala Pro Tyr
        115

<210> SEQ ID NO 4
<211> LENGTH: 117

```
<212> TYPE: PRT
<213> ORGANISM: Artificial Sequence
<220> FEATURE:
<223> OTHER INFORMATION: Synthetic- PDL1D (D26E, Y56I, V68I, S117I,
      D122E, Y123W and R125M) peptide

<400> SEQUENCE: 4

Ala Phe Thr Val Thr Val Pro Lys Glu Leu Tyr Val Glu Tyr Gly
 1               5                   10                  15

Ser Asn Met Thr Ile Glu Cys Lys Phe Pro Val Glu Lys Gln Leu Asp
             20                  25                  30

Leu Ala Ala Leu Ile Val Ile Trp Glu Met Glu Asp Lys Asn Ile Ile
         35                  40                  45

Gln Phe Ile His Gly Glu Glu Asp Leu Lys Val Gln His Ser Ser Tyr
     50                  55                  60

Arg Gln Arg Ala Arg Leu Leu Lys Asp Gln Leu Ser Leu Gly Asn Ala
65                  70                  75                  80

Ala Leu Gln Ile Thr Asp Val Lys Leu Gln Asp Ala Gly Val Tyr Arg
             85                  90                  95

Cys Met Ile Ile Tyr Gly Gly Ala Glu Trp Lys Met Ile Thr Val Lys
            100                 105                 110

Val Asn Ala Pro Tyr
        115

<210> SEQ ID NO 5
<211> LENGTH: 504
<212> TYPE: DNA
<213> ORGANISM: Artificial Sequence
<220> FEATURE:
<223> OTHER INFORMATION: Synthetic- PDL1A vector insert with AviTag and
      6X His tag

<400> SEQUENCE: 5
gccaccatgg actggacttg gagaatcctg tttctcgtag ctgctgcaac tggagcacac      60
tccgccttca ccgtgaccgt gcccaaggac ctgtacgtgg tggagtacgg cagcaacatg    120
accatcgagt gcaagttccc cgtggagaag cagctggacc tggccgccct gatcgtgtac    180
tgggagatgg aggacaagaa catcatccag ttcgtgcacg gcgaggagga cctgaaggtg    240
cagcacagca gctaccggca gcgggcccgg ctgctgaagg accagctgag cctgggcaac    300
gccgccctgc agatcaccga cgtgaagctg caggacgccg gcgtgtaccg gtgcatgatc    360
agctacggcg gcgccgactg gaagcggatc accgtgaagg tgaacgcctc aggaggcgga    420
ggctcaggag gcgaggcgg cctgaacgac atcttcgagg cccagaagat cgagtggcac    480
gagcatcatc accatcacca ctag                                          504

<210> SEQ ID NO 6
<211> LENGTH: 504
<212> TYPE: DNA
<213> ORGANISM: Artificial Sequence
<220> FEATURE:
<223> OTHER INFORMATION: Synthetic- PDL1C vector insert with AviTag and
      6X His tag

<400> SEQUENCE: 6
gccaccatgg actggacttg gagaatcctg tttctcgtag ctgctgcaac tggagcacac      60
tccgccttca ccgtgaccgt gcccaaggac ctgtacgtgg tggagtacgg cagcaacatg    120
accatcgagt gcaagttccc cgtggagaag cagctggacc tggccgccct gatcgtgatc    180
tgggagatgg aggacaagaa catcatccag ttcatccacg gcgaggagga cctgaaggtg    240
```

```
cagcacagca gctaccggca gcgggcccgg ctgctgaagg accagctgag cctgggcaac    300
gccgccctgc agatcaccga cgtgaagctg caggacgccg gcgtgtaccg gtgcatgatc    360
atctacggcg gcgccgactg gaagcggatc accgtgaagg tgaacgcctc aggaggcgga    420
ggctcaggag gcggaggcgg cctgaacgac atcttcgagg cccagaagat cgagtggcac    480
gagcatcatc accatcacca ctag                                           504

<210> SEQ ID NO 7
<211> LENGTH: 504
<212> TYPE: DNA
<213> ORGANISM: Artificial Sequence
<220> FEATURE:
<223> OTHER INFORMATION: Synthetic- PDL1D vector insert with AviTag and
      6X His tag

<400> SEQUENCE: 7
gccaccatgg actggacttg gagaatcctg tttctcgtag ctgctgcaac tggagcacac     60
tccgccttca ccgtgaccgt gcccaaggag ctgtacgtgg tggagtacgg cagcaacatg    120
accatcgagt gcaagttccc cgtggagaag cagctggacc tggccgccct gatcgtgatc    180
tgggagatgg aggacaagaa catcatccag ttcatccacg gcgaggagga cctgaaggtg    240
cagcacagca gctaccggca gcgggcccgg ctgctgaagg accagctgag cctgggcaac    300
gccgccctgc agatcaccga cgtgaagctg caggacgccg gcgtgtaccg gtgcatgatc    360
atctacggcg gcgccgagtg gaagatgatc accgtgaagg tgaacgcctc aggaggcgga    420
ggctcaggag gcggaggcgg cctgaacgac atcttcgagg cccagaagat cgagtggcac    480
gagcatcatc accatcacca ctag                                           504
```

RECOMBINANT PD-L1 PEPTIDES AND METHODS OF USE

CROSS-REFERENCE TO RELATED APPLICATIONS

This application represents the national stage entry of PCT/US2020/028145 filed on Apr. 14, 2020 and claims priority to U.S. Provisional Application No. 62/834,242 filed on Apr. 15, 2019, the contents of which are incorporated by reference in its entirety.

STATEMENT REGARDING FEDERALLY SPONSORED RESEARCH

N/A

SEQUENCE LISTING

A Sequence Listing accompanies this application and is submitted as an ASCII text file of the sequence listing named "2020-02-14_650053.00672_ST25.txt" which is 7.28 KB in size and was created on Feb. 14, 2020. The sequence listing is electronically submitted via EFS-Web with the application and is incorporated herein by reference in its entirety.

BACKGROUND OF THE INVENTION

The field of the invention is related to mutant PD-L1 peptides and methods for generating regulatory T cells.

According to epidemiological data, the incidence of autoimmune diseases, including Type 1 diabetes (T1D), has steadily increased in the United States and throughout the world in the last few decades. Development of an autoimmune disease is characterized by a breakdown of immune tolerance mechanisms, leading to an imbalance between autoreactive CD4+ effector T (Th1) cells and Foxp3+ regulatory T (Treg) cells. In T1D, this impairment leads to T cell-mediated destruction of pancreatic β cells, progressive decline in insulin secretion, and, ultimately, an inability to regulate blood glucose homeostasis. Though T1D can be managed by regularly monitoring blood glucose levels and administering exogenous insulin, patients are still susceptible to complications from fluctuations in blood glucose, as insulin replacement therapy is not as efficient for blood glucose control as natural secretion. Thus, a better way to slow the progress of T1D would be to maintain natural insulin secretion by reducing the destruction of pancreatic β cells. Accordingly, there is a need in the art for methods that restore immune tolerance and, therefore, preserve cells targeted by autoimmune disease.

SUMMARY OF THE INVENTION

The present disclosure provides soluble mutant PD-L1 peptides that consist essentially of the amino acid sequence AFTVTVPKDLYVVEYGSNMTIECKFPVEKQLDLAA-LIVYWEMEDKNIIQFVHGEEDLKVQ HSSYRQRARLLKDQLSLG-NAALQITDVKLQDAGVYRCMISYGGA-DYKRITVKVNAPY (corresponding to amino acids 18-132; SEQ ID NO: 1), wherein the mutant PD-L1 peptide comprises one or more mutations selected from the group consisting of D26E, D122E, Y123W, R125M, Y56I, S117I, V68I and combinations thereof, and wherein the numbering of amino acid sequence begins at 18.

In another aspect, the present disclosure provides polynucleotides encoding the soluble mutant PD-L1 peptides disclosed herein.

In another aspect, the present disclosure provides vectors capable of expressing the soluble mutant PD-L1 peptides. The vectors comprise a promoter operably connected to polynucleotides encoding the soluble mutant PD-L1 peptides disclosed herein.

In another aspect, the present disclosure provides host cells comprising the vectors disclosed herein.

In another aspect, the present disclosure provides soluble mutant PD-L1 peptide-bead complexes. The complexes comprise the soluble mutant PD-L1 peptides disclosed herein and a bead, wherein the peptide is covalently or non-covalently attached to the bead.

In a final aspect, the present disclosure provides methods of generating regulatory T cells (Foxp3+Tregs). The methods comprise contacting Th1 cells with a soluble mutant PD-L1 peptide disclosed herein in an amount effective to generate Treg cells.

DETAILED DESCRIPTION OF THE INVENTION

The present invention provides mutant peptides and variants, nucleic acid sequences and vectors encoding the mutant peptides, compositions containing the mutant peptides (and in some instances specific combinations of two or more peptides) or vectors, s and methods of using them to elicit regulatory T cells and produce T cell populations, all detailed below.

Many autoimmune diseases, included type I diabetes (T1D), are characterized by the breakdown of immune tolerance mechanisms, leading to an imbalance between autoreactive CD4+ effector T (Th1) cells and regulatory (Treg) T cells. Treg cells, which are characterized by expression of the transcription factor Foxp3, play a central role in maintaining peripheral tolerance. In fact, studies have revealed a correlation between a decrease in functional Treg cells in patients and the incidence of human autoimmune diseases. Thus, one strategy to regulate autoimmune reactions is to shift the balance back from CD4+ effector T cells to Foxp3+Treg cells. Several clinical trials are currently attempting to produce this shift in patients with autoimmune diseases by infusing them with Treg cells. The Treg cells used in such applications must be isolated from peripheral or umbilical cord blood and enriched or expanded under good manufacturing practice (GMP) conditions. However, Treg cells comprise just 5-10% of all circulating CD4+T cells, making the isolation of large quantities of Treg cells challenging. While technical advances have recently made it possible to expand Treg cells ex-vivo in 20-36 days, methods that are more efficient are needed.

In previous work, the inventors discovered that conventional T cells overexpressing PD-L1 via a lentiviral vector were able to convert T helper type 1 (Th1) cells into Treg through the induction of the PD1/PD-L1 co-inhibitory pathway. In the present disclosure, the inventors build upon this discovery by creating novel mutant truncated PD-L1 peptides that facilitate Treg differentiation. Thus, these mutant PD-L1 peptides may be used to efficiently produce large quantities of Treg cells ex-vivo.

Figure 1A:
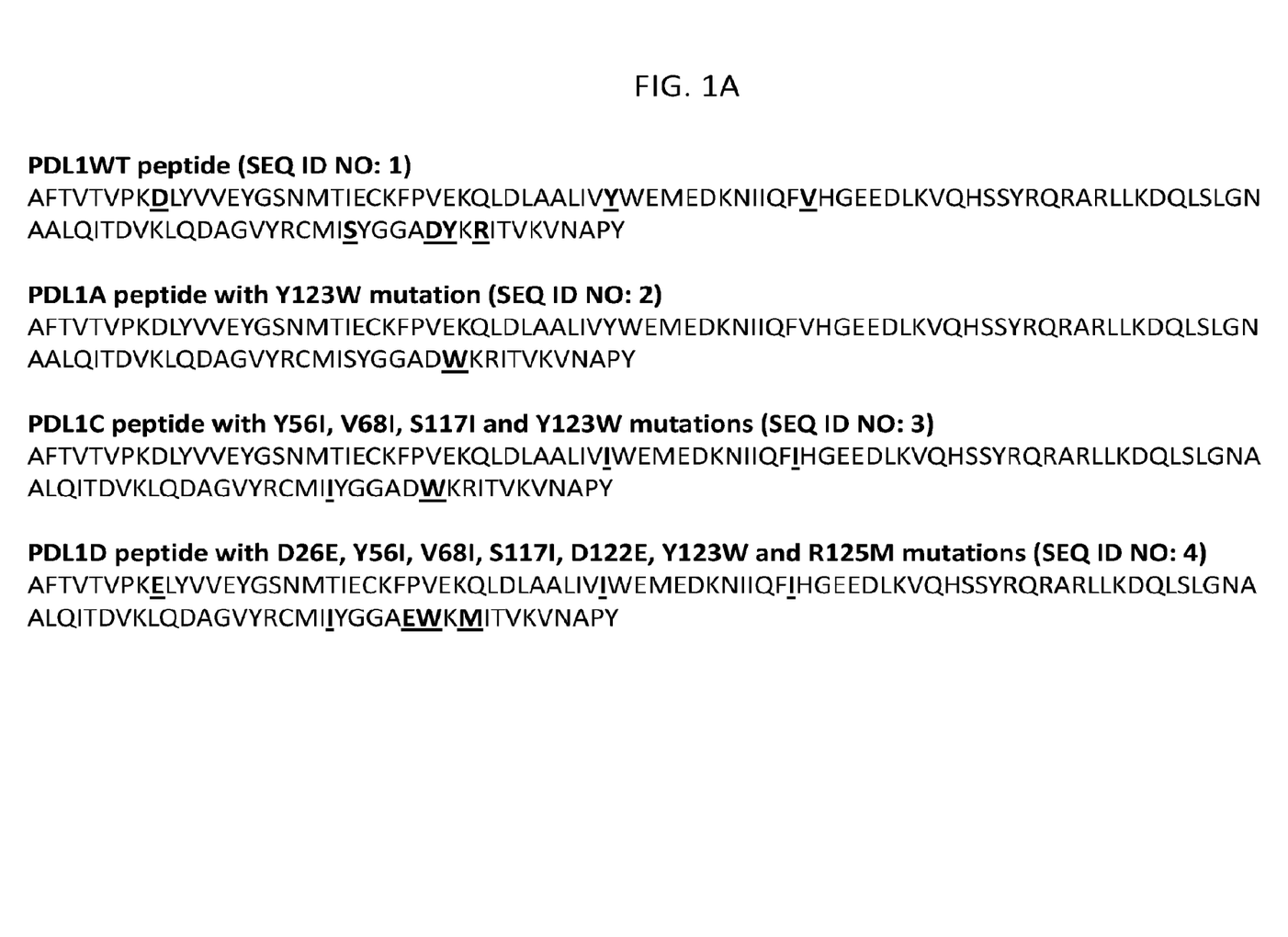
FIG. 1A shows the sequences of the truncated PD-L1 peptides (which corresponds to amino acids 18-132 of the full-length protein). The top sequence is the wild-type peptide (PDL1WT). The amino acids residues that are mutated in the mutant PD-L1 peptides are bolded and underlined in the wild-type sequence. Below are the sequences of the three mutant PD-L1 peptides: PDL1 A, PDL1 C, and PDL1D.
Figure 1B:
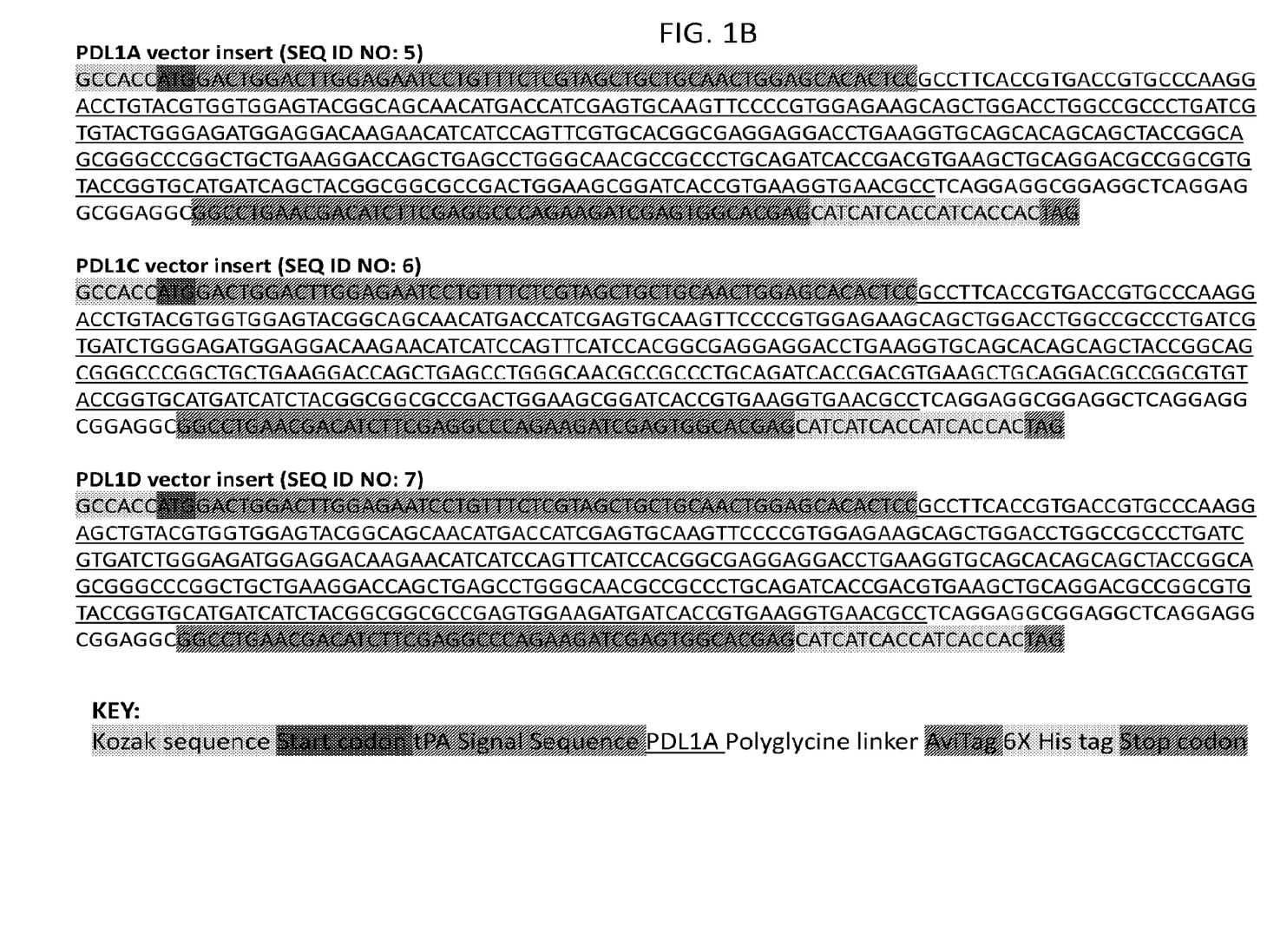
FIG. 1B shows the DNA sequences that were inserted into the pcDNA™ 3.4 TOPO® vector for expression of the mutant PD-L1 peptides. The insert comprises sequences encoding the tissue plasminogen activator (tPA) signal sequence, a mutant peptide, a polyglycine linker, an Avi-Tag™, and a 6X His tag. These features are color coded, as indicated in the key.

As is described in the Examples, several point mutations were engineered into a truncated version of the PD-L1 protein (see FIG. 1A). Wild-type (WT) and mutant PD-L1 peptides were produced using a mammalian expression system (Gibco Expi293 Expression system, Thermo Fisher Scientific), were purified using nickel affinity chromatography, and were biotinylated using an enzymatic reaction. Biotinylated PD-L1 protein was subsequently captured using streptavidin-coated magnetic beads and incubated with primary human Th1 cells. Two days later, the cells were analyzed by western blot and flow cytometry for expression of Treg- and Th1-specific transcription factors (Foxp3 and Tbet, respectively). This analysis showed that expression of Foxp3 was significantly increased in cells incubated with mutant PD-L1-coated beads, while that of Tbet was significantly reduced, suggesting that the truncated PD-L1 constructs disclosed herein are able to direct Th1 cells to differentiate into Treg cells.

Compositions

The present invention provides soluble mutant PD-L1 peptides. As used herein, the terms "proteins," "peptides" and "polypeptides" are used interchangeably herein to designate a series of amino acid residues connected to the other by peptide bonds between the alpha-amino and carboxy groups of adjacent residues. "Protein" and "polypeptide" are often used in reference to relatively large polypeptides, whereas the term "peptide" is often used in reference to small polypeptides, but usage of these terms in the art overlaps. Proteins may include modified amino acids (e.g., phosphorylated, glycated, glycosylated, etc.) and amino acid analogs.

In all embodiments, the mutant PD-L1 peptides are soluble peptides. The mutant peptides were engineered from a truncated version of PD-L1 the PD-L1 protein, which corresponds to amino acids 18-132 of the full-length protein. This truncated PD-L1 peptide is soluble and does not contain the transmembrane domain of wildtype PD-L1. Thus, as used herein, the term "soluble peptide" refers to a peptide that is truncated as to omit membrane-spanning domains that are present in the naturally occurring, non-soluble form.

The mutant PD-L1 peptides described herein have at least one amino acid mutation as compared with the corresponding wild-type sequence of the truncated PD-L1 protein. As used herein, the term "at least one mutation" includes one or more substitutions within the contemplated peptides that improve the efficacy of the PD-L1 peptides to direct Th1 cells to differentiate to Treg cells in culture. The mutant PD-L1 peptides consist essentially of the amino acid sequence AFTVTVPK<u>D</u>LYVVEYGSNMTIECKFPVEKQLDLAALIVYWEME<u>D</u>KNIIQFVHGEEDLKVQ HSS<u>Y</u>RQ<u>R</u>ARLLK<u>D</u>QLSLG-NAALQITDVKLQDAGVYRCM<u>I</u>SYGGA<u>D</u>YKRITVKV-NAPY (SEQ ID NO: 1; amino acids 18-132 of the full-length PD-L1 protein), and comprise one or more mutations at the underlined and bolded amino acid residues as compared to the wild-type sequence. Preferably, the mutant PD-L1 peptides comprise two or more mutations, alternatively three or more mutations, alternatively four or more mutations, alternatively five or more mutation, alternatively 6 or more mutations, alternatively all seven amino acids are mutated to a non-wild-type amino acid. Suitable mutations include D26E, D122E, Y123W, R125M, Y56I, S117I, V68I and combinations thereof. For clarity, the numbering of these mutations refers to the amino acid position in the full-length PD-L1 sequence, and the mutant peptides of the present disclosure start at amino acid 18 of the full-length PD-L1 protein. As such, in the amino acid sequence listed above, the first "A" is amino acid 18 and the last "Y" is amino acid 132. Thus, for example, mutation D26E refers to the first underlined "D" in the above sequence, D122E refers to the fifth underlined amino acid in the above sequence, etc. One skilled in the art would understand how to produce mutant PD-L1 peptides consisting of one or more of the disclosed mutations (i.e., D26E, D122E, Y123W, R125M, Y56I, S117I, V68I) within the provided truncated PD-L1 peptide. For example, the present invention provides a mutant PD-L1 consisting of the the amino acid sequence AFTVTVPK<u>D</u>LYVVEYGSNMTIECKFPVEKQLDLAALIV<u>Y</u>WEME<u>D</u>KNIIQFV<u>H</u>GEEDLKVQ HSS<u>Y</u>RQ<u>R</u>ARLLK<u>D</u>QLSLG-NAALQITDVKLQDAGVYRCM<u>I</u>SYGGA-<u>D</u>YKRITVKVNAPY (SEQ ID NO: 1) and one or more of the mutations selected from D26E, D122E, Y123W, R125M, Y56I, S117I, V68I and combinations thereof; suitably, two or more mutations selected from D26E, D122E, Y123W, R125M, Y56I, S117I, V68I and combinations thereof; suitably, three or more mutations selected from D26E, D122E, Y123W, R125M, Y56I, S117I, V68I and combinations thereof; suitably, four or more mutations selected from D26E, D122E, Y123W, R125M, Y56I, S117I, V68I and combinations thereof; suitably, five or more mutations selected from D26E, D122E, Y123W, R125M, Y56I, S117I, V68I and combinations thereof; suitably, six or more mutations selected from D26E, D122E, Y123W, R125M, Y56I, S117I, V68I and combinations thereof; or suitably, the mutant PD-L 1 peptide comprises all seven (7) mutations D26E, D122E, Y123W, R125M, Y56I, S117I, V68I.

In the examples, the inventors test the ability of three mutant PD-L1 peptides (referred to as PDL1A, PDL1C, and PDL1D) to direct Th1 cell differentiation. PDL1A is amino acids 18-132 of PD-L1 with the Y123W mutation (SEQ ID NO: 2). PDL1C is amino acids 18-132 of PD-L1 with the Y56I, V68I, S117I, and Y123W mutations (SEQ ID NO: 3). PDL1D is amino acids 18-132 of PD-L1 with the D26E, D122E, Y123W, R125M, Y56I, S117I, V68I mutations (SEQ ID NO: 4). The sequences of these peptides are shown in FIG. 1A.

In some embodiments, the mutant PD-L1 peptides described herein further comprise an exogenous tag or agent. The term "tag" or "agent" as used herein includes any useful moiety that allows for the purification, identification, detection, or therapeutic use of the mutant peptides of the present invention. Any tag or agent that does not interfere with the functionality of the mutant PD-L1 peptides may be used with the present invention. Suitable tags are known in the art and include, but are not limited to, affinity or epitope tags (e.g., cMyc, HIS, FLAG, V5-tag, HA-tag, NE-tag, S-tag, Ty tag, etc) and florescence tags (e.g., RFP, GFP, etc). Epitope tags are commonly used as a "purification tag", i.e. a tag that facilitates isolation of the polypeptide from other non-specific proteins and peptides. For instance, the inventors included a 6X His tag in the mutant peptides to allow them to be purified by nickel affinity chromatography using standard methods known in the art. In some embodiments, the tag is a polypeptide and the mutant PD-L1 peptide and the tag are encoded in one nucleic acid sequence and translated concurrently. In some embodiments, the tag is cleavable and can be removed once the peptide is made and purified.

The mutant PD-L1 peptides may be linked directly, linked indirectly, or conjugated to the tag or agent. As used herein, the term "conjugate" refers to the joining of two entities by covalent bonds. The entities may be covalently bonded directly or through linking groups using standard synthetic coupling procedures. For example, two polypeptides may be linked together by simultaneous polypeptide expression, forming a fusion or chimeric protein. One or more amino acids may be inserted into the polypeptide to serve as a linking group (i.e., via incorporation of corresponding nucleic acid sequences into the vector). For example, in some embodiments, a polyglycine linker is included between the mutant PD-L1 peptide sequence and a tag (see FIG. 1B). Other contemplated linking groups include polyethylene glycols or hydrocarbons terminally substituted with amino or carboxylic acid groups to allow for amide coupling with polypeptides having amino acids side chains with carboxylic acid or amino groups, respectively. Alternatively, the amino and carboxylic acid groups can be substituted with other binding partners, such as an azide and an alkyne groups, which undergo copper catalyzed formation of triazoles.

In some embodiments, the mutant PD-L1 peptides comprise multiple tags. For example, a second tag may be included to allow for easy capture of the mutant peptides. The inventors expressed the mutant PD-L1 peptides as fusion proteins that comprised both a 6X His tag and an AviTag™ (GeneCopoeia). The AviTag™ is a 15 amino acid peptide that is biotinylated by biotin ligase in the presence of biotin and ATP. By including an AviTag™ in the mutant PD-L 1 peptides, the inventors were able to biotinylate the purified peptides, allowing them to capture the peptides using streptavidin-coated beads. Many other suitable agent/tag capture methods are known to those skilled in the art and are considered disclosed herein.

In some embodiments, the mutant PD-L1 peptides comprise additional amino acid sequences. For example, to increase secreted protein expression, the inventors included a tissue plasminogen activator (tPA) signal sequence as a leader sequence in the mutant peptides. However, there are many other heterologous sequences that may be included in the peptides of the present invention to enhance their expression or purification. Exemplary sequences comprising mutant PD-L1 peptides along with the tPA signal sequence, a polyglycine linker, an AviTag™, and a 6X His tag are shown in FIG. 1B. One of skill in the art will understand that such sequences should be selected with the particular expression and purification systems that will be utilized in mind.

The present disclosure also provides polynucleotides encoding the soluble mutant PD-L1 peptides disclosed herein. The terms "polynucleotide," "polynucleotide sequence," "oligonucleotide," "nucleic acid," and "nucleic acid sequence" are used interchangeably herein to refer to nucleotide sequences or fragments thereof. These phrases may refer to DNA or RNA of genomic, natural, or synthetic origin, and include single-stranded or double-stranded molecules, as well as sense or antisense strands of such molecules.

The present disclosure also provides vectors capable of expressing the soluble mutant PD-L1 peptides described herein. Suitable vectors for use with the present invention comprise a promoter operably connected to a polynucleotide sequence encoding a mutant PD-L1 peptides described herein. The vectors may also comprise appropriate control sequences that allow for translational regulation in a host cell. In some embodiments, the vectors further comprise the nucleic acid sequences for one or more agents or tags. In some embodiments, the vectors further comprise additional regulatory sequences, such as signal sequences.

As used herein, the term "vector" refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors" (or simply, "vectors"). The term vector encompasses "plasmids", the most commonly used form of vector. Plasmids are circular double-stranded DNA loops into which additional DNA segments (e.g., those encoding mutant PD-L1 peptides) may be ligated. However, other forms of expression vectors, such as viral vectors (e.g., replication defective retroviruses, adenoviruses and adeno-associated viruses), may also be used with the present invention. Certain vectors are capable of autonomous replication in a host cell into which they are introduced (e.g., bacterial vectors having a bacterial origin of replication and episomal mammalian vectors). Other vectors may be integrated into the genome of a host cell upon introduction into the host cell, and are thereby replicated along with the host genome. In one specific embodiment, the vectors comprise the pcDNA™ 3.4 TOPO® (Thermo Fisher Scientific), a constitutive mammalian expression vector that was designed to deliver high levels of transgene expression.

In some embodiments, the vector is a mini-circle DNA (mcDNA) vector. Mini-circle DNA vectors are episomal DNA vectors that are produced as circular expression cassettes devoid of any bacterial plasmid DNA backbone. See, e.g. System Biosciences, Mountain View Calif., MN501A-1. Their smaller molecular size enables more efficient transfections and offers sustained expression over a period of weeks as compared to standard plasmid vectors that only work for a few days. The mini-circle constructs may be derived from a plasmid with a bacterial origin of replication and optionally antibiotic resistance genes flanked by att sites (i.e., to allow for recombination and exclusion of the DNA between the att sites and formation of the mini-circle vector).

In some embodiments, the vectors of the present invention further comprise heterologous backbone sequence. As used herein, "heterologous nucleic acid sequence" refers to a non-human nucleic acid sequence, for example, a bacterial, viral, or other non-human nucleic acid sequence that is not naturally found in a human. Heterologous backbone sequences may be necessary for propagation of the vector and/or expression of the encoded peptide. Many commonly used expression vectors and plasmids contain non-human nucleic acid sequences, including, for example, CMV promoters.

Suitable promoters for the practice of the present invention include, without limitation, constitutive, inducible, temporally regulated, developmentally regulated, chemically regulated, physically regulated (e.g., light regulated or temperature-regulated), tissue-preferred, and tissue-specific promoters. Promoters may include pol I, pol II, or pol III promoters. Suitable promoters include "heterologous promoters", a term that refers to any promoter that is not naturally associated with a polynucleotide to which it is operably connected. In mammalian cells, typical promoters include, without limitation, promoters for Rous sarcoma virus (RSV), human immunodeficiency virus (HIV-1), cytomegalovirus (CMV), SV40 virus, and the like as well as the translational elongation factor EF-1α promoter or ubiquitin promoter. Those of skill in the art are familiar with a wide variety of additional promoters for use in various cell types.

Protein and nucleic acid sequence identities are evaluated using the Basic Local Alignment Search Tool ("BLAST") which is well known in the art (Karlin and Altschul, 1990, *Proc. Natl. Acad. Sci.* USA 87: 2267-2268; Altschul et al., 1997, *Nucl. Acids Res.* 25: 3389-3402). The BLAST programs identify homologous sequences by identifying similar segments, which are referred to herein as "high-scoring segment pairs," between a query amino or nucleic acid sequence and a test sequence which is preferably obtained from a protein or nucleic acid sequence database. Preferably, the statistical significance of a high-scoring segment pair is evaluated using the statistical significance formula (Karlin and Altschul, 1990), the disclosure of which is incorporated by reference in its entirety. The BLAST programs can be used with the default parameters or with modified parameters provided by the user.

"Percentage of sequence identity" or "percent similarity" is determined by comparing two optimally aligned sequences over a comparison window, wherein the portion of the polynucleotide or peptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "substantial similarity" of polynucleotide or peptide sequences means that a polynucleotide or peptide comprises a sequence that has at least 75% sequence identity. Alternatively, percent identity can be any integer from 75% to 100%. More preferred embodiments include at least: 75%, 80%, 85%, 86%, 87%, 88%, 89%, 90%, 91%, 92%, 93%, 94%, 95%, 96%, 97%, 98% or 99% compared to a reference sequence using the programs described herein; preferably BLAST using standard parameters, as described. These values can be appropriately adjusted to determine corresponding identity of proteins encoded by two nucleotide sequences by taking into account codon degeneracy, amino acid similarity, reading frame positioning and the like.

"Substantial identity" of amino acid sequences for purposes of this invention normally means polypeptide sequence identity of at least 75%. Preferred percent identity of polypeptides can be any integer from 75% to 100%. More preferred embodiments include at least 75%, 80%, 85%, 86%, 87%, 88%, 89%, 90%, 91%, 92%, 93%, 94%, 95%, 96%, 97%, 98%, 98.7%, or 99%.

The present disclosure also provides compositions comprising the mutant PD-L1 peptides and a pharmaceutically acceptable carrier. The pharmaceutically acceptable carrier should be selected based on the selected route of administration and standard pharmaceutical practice. The composition may be formulated into dosage forms according to standard practices in the field of pharmaceutical preparations (See Alphonso Gennaro, ed., Remington's Pharmaceutical Sciences, 18th Ed., (1990) Mack Publishing Co., Easton, Pa.). Suitable dosage forms may comprise, for example, solutions, parenteral solutions, or suspensions. In some embodiments, the composition comprises an isolated and purified mutant PD-L1 peptide described herein. In other embodiments, the composition comprises an isolated and purified polypeptide or vector comprising the nucleic acid sequences encoding a mutant PD-L1 peptide described herein.

In another aspect, the present disclosure provides host cells comprising the vectors described herein. Any host cell that allows for expression of the mutant PD-L1 peptides encoded by the vectors may be used with the present invention. For example, common host cells include bacteria (e.g., *E. coli, B. subtilis*), yeast (e.g., *S.cerevisiae*) or eukaryotic cell lines. Advantageously, insect or mammalian cell lines may be used to provide human-like splicing of mRNA. In the Examples, the inventors utilized the Gibco Expi293 Expression System (Thermo Fisher Scientific) to express the mutant PD-L1 peptides in human embryonic kidney 293 cells. This system allows for large-scale transfection of 293 cells in suspension culture for maximum protein yield. However, those of skill in the art are aware that many expression systems and cell lines may be used to express the peptides of the present invention, including many that are commercially available.

In yet another aspect, the present disclosure provides mutant PD-L1 peptide-bead complexes, in which a mutant PD-L1 peptide described herein is covalently or non-covalently attached to the beads. Suitable methods of conjugating or attaching the mutant PD-L1 peptides to beads are known in the art. For example, in one embodiment, the mutant PD-L1 peptide further comprises a tag that is capable of being biotinylated (e.g., an AviTag™). To form peptide-bead complexes, the tag is biotinylated using an enzymatic reaction after the peptide has been purified, and the biotinylated peptide is incubated with beads that are coated in streptavidin. Suitable streptavidin-coated beads are known in the art and include, for example, Dynabeads® (ThermoFisher Scientific).

Methods

The present disclosure provides methods of generating regulatory T cells (Foxp3$^+$ Tregs). The methods involve contacting Th1 cells with a soluble mutant PD-L1 peptide described herein in an amount effective to generate Treg cells. Methods of "contacting" the cell with the peptide are known in the art and include, for example, in vitro culturing the Th1 cells in medium comprising the soluble mutant PD-L1 peptide or beads coated with the mutant PD-L1 peptide. Other methods of contacting include, for example, in vivo administering the soluble mutant PD-L1 peptide.

The present disclosure also provides methods of altering the Th1/Treg cell balance, the method comprising contacting the T cells with a sufficient amount of the mutant PD-L1 peptide described herein to differentiate the Th1 cell into a T-regulatory cell. Suitably, the methods increase the number of Treg cells and decrease the number of Th1 cells in a system. In a preferred embodiment, the method is carried out in vitro under tissue culture conditions. In another embodiment, the method is carried out in vivo by administering the mutant PD-L1 peptide, composition or vector to a subject in need of T cell regulation.

In further aspects, methods of preventing, reducing or slowing the progression or development of autoimmune disease (e.g., type I diabetes). The method comprises administering a therapeutically effective amount of PD-L1 mutant peptides described herein to increase the Treg cells within the subject.

The terms "effective amount" or "therapeutically effective amount" refer to an amount sufficient to effect beneficial or desirable biological and/or clinical results. For example, therapeutically effective amounts of the peptides of the instant invention may be combined with a pharmaceutically acceptable carrier to form a composition. The composition can be administered in any of the art-recognized modes. The doses, methods of administration, and suitable pharmaceutically acceptable carriers, diluents, and excipients for use with such methods can readily be determined by a skilled artisan, but will depend on the particular circumstances at hand.

Appropriate dosages may be determined, for example, by extrapolation from animal studies or in clinical trials taking into account body weight of the patient, absorption rate, half-life, disease severity and the like. The number of doses and course of treatment may be varied from individual to individual. In some embodiments for the prevention of the development or progression of an autoimmune disease, booster dosages may be required. Suitable booster schedules may be determined by a skilled artisan. For example, the peptides or vectors may be given every month, every other month, every 4 months, every 6 months, once a year, once every two years, and any range of time in between.

The composition is preferably in unit dosage form. In such form, the preparation is divided into unit doses containing appropriate quantities of the active component. The unit dosage form can be a packaged preparation, the package containing discrete quantities of preparation, such as packeted tablets, capsules, and powders in vials or ampoules. In addition, the unit dosage form can be a capsule, tablet, cachet, or lozenge itself, or it can be the appropriate number of any of these in packaged form.

As used herein, "subject" or "patient" refers to both mammals and non-mammals. "Mammals" include any member of the class Mammalia, such as humans, non-human primates (e.g., chimpanzees, other apes and monkey species), farm animals (e.g., cattle, horses, sheep, goats, and swine), domestic animals (e.g., rabbits, dogs, and cats), and laboratory animals (e.g., rats, mice, and guinea pigs). Examples of non-mammals include, but are not limited to, birds. The term "subject" does not denote a particular age or sex. In one embodiment, the subject is a human. In a particular embodiment, the human is a human suffering from an autoimmune disease, e.g., type I diabetes.

As used herein, the terms "administering" and "administration" refer to any method of providing a pharmaceutical preparation or composition to a subject comprising the recombinant PD-L1 peptides described herein. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, intradermal administration, intrathecal administration and subcutaneous administration. Administration can be continuous or intermittent. In various aspects, a preparation can be administered therapeutically; that is, administered to treat an existing disease or condition.

To aid in administration, the peptides or vectors may be mixed with a suitable carrier or diluent such as water, oil (e.g., a vegetable oil), ethanol, saline solution (e.g., phosphate buffer saline or saline), aqueous dextrose (glucose) and related sugar solutions, glycerol, or a glycol such as propylene glycol or polyethylene glycol. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl-or propyl-paraben, and chlorbutanol. The composition for parenteral administration may take the form of an aqueous or nonaqueous solution, dispersion, suspension or emulsion.

For purposes of the present invention, "treating" or "treatment" describes the management and care of a subject for the purpose of combating the disease, condition, or disorder. Treating includes the administration of a mutant PD-L1 peptide of present invention to reduce, inhibit or prevent the onset of the symptoms or complications, reduce or alleviating the symptoms or complications, or eliminating the disease, condition, or disorder. In a preferred embodiment, the disease is an autoimmune disease. In a particular embodiment, the autoimmune disease is type 1 diabetes (T1D).

Aspects of the disclosure described with respect to the former method can be applicable to the latter method and kits, and vice versa, unless the context clearly dictates otherwise.

Suitable kits are also included for preforming the methods described herein. Kits may comprises a mutant PD-L1 peptide as described herein or compositions comprising the mutant PD-L1 peptide and instructions for the use. Kits comprising beads coated or covalently linked to the mutant peptides described herein are also provided.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. For example, with regard to sequences "consisting of" refers to the sequence listed in the SEQ ID NO. and does refer to larger sequences that may contain the SEQ ID as a portion thereof.

All publications, patent applications, patents, and other references mentioned herein are incorporated by reference in their entirety. In the case of conflict, the present specification, including definitions, will control.

Other features and advantages of the invention will be apparent from the description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting.

Examples

Example 1: Induction of Treg Cells with Truncated Mutant PD-L1 Peptides

The present inventors have designed truncated, mutant PD-L1 peptides that contain one or more mutation as compared with the corresponding wild-type sequence (shown in FIG. 1A). These peptides contain both a polyhistidine tag and an AviTag™ to facilitate their purification and capture, respectively. For peptide expression, the DNA sequences encoding the mutant PD-L1 peptides were cloned into a pcDNA™3.4 vector using the pcDNA™3.4 TOPO™ TA Cloning Kit (Thermo Fisher Scientific, catalog #A14697).

Mutant PD-L1 peptides were produced and purified using standard methods known in the art. Briefly, the peptides were expressed using a mammalian expression system (Gibco Expi293 Expression system, Thermo Fisher Scientific), purified using nickel affinity chromatography, and biotinylated in an enzymatic reaction. The biotinylated PD-L1 protein was then immobilized onto streptavidin-coated Dynabeads.

Figure 2:
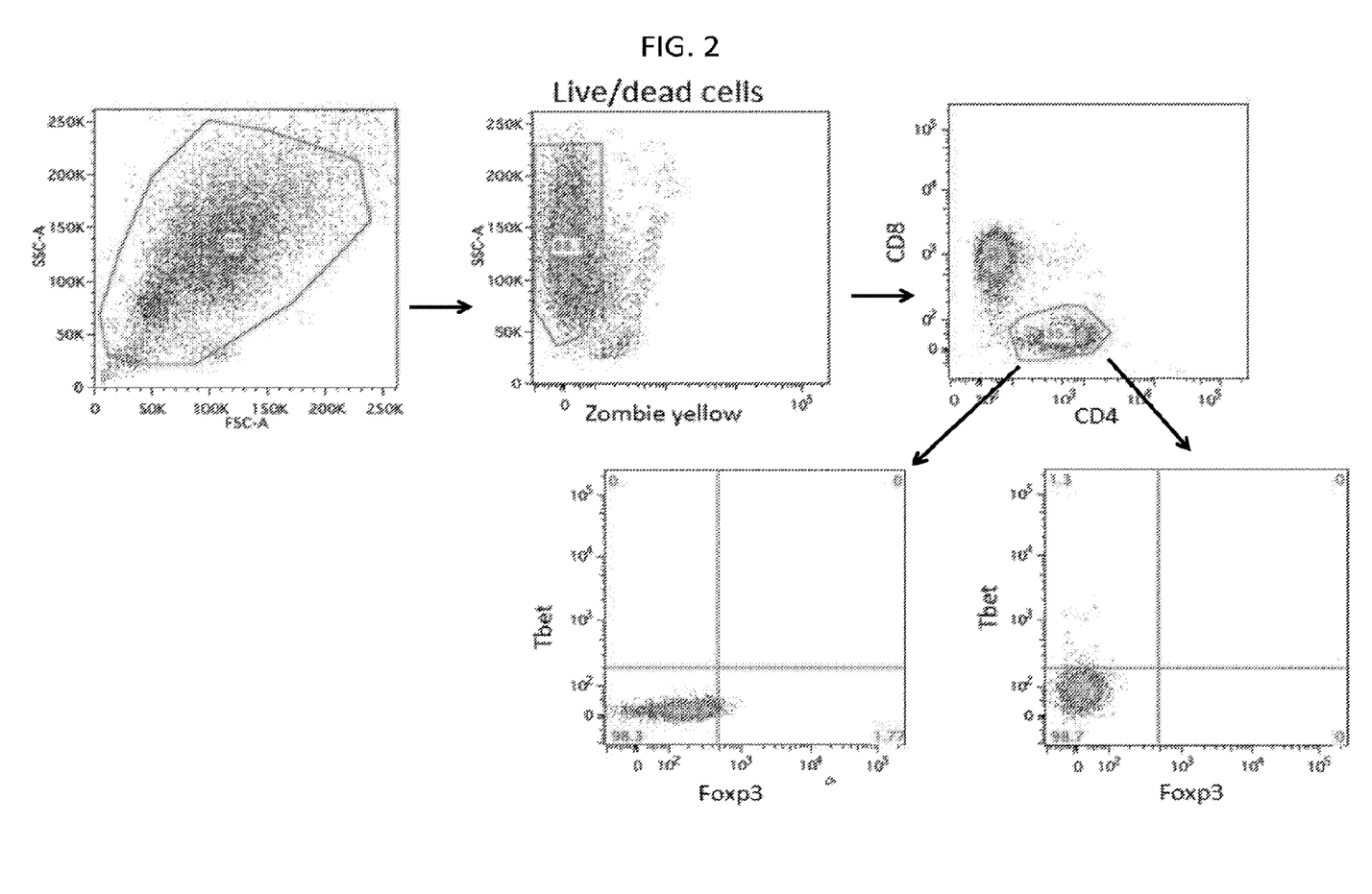
FIG. 2 is a schematic of the flow cytometry analysis for expression of Treg- and Th1-specific transcription factors (Foxp3 and Tbet, respectively).
Figure 3:
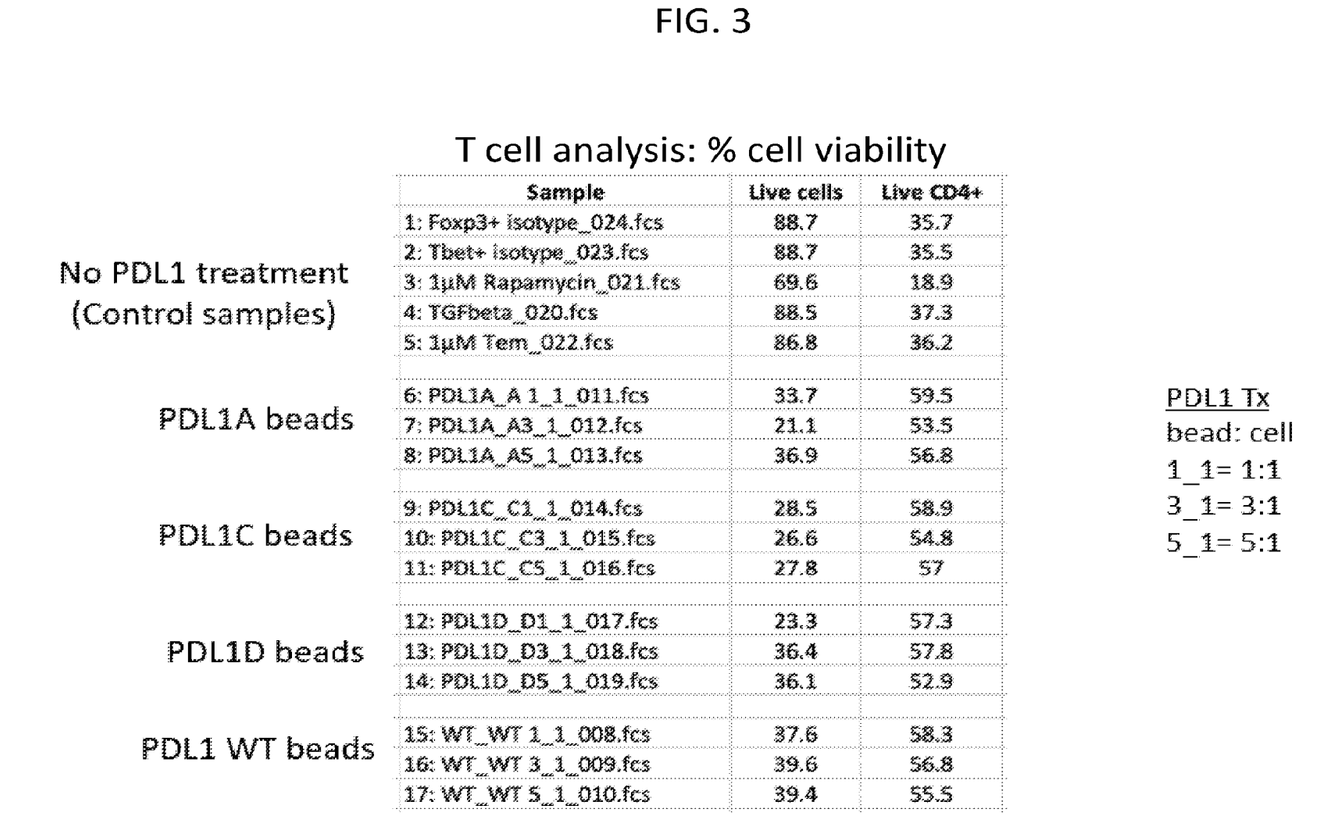
FIG. 3 shows the percent cell viability of T cells treated with beads coated with the mutant PD-L1 peptides (PDL1A, PDL1C and PDL1D) as compared to those treated with the wildtype PD-L1 peptide (PDL1WT).
Figure 4:
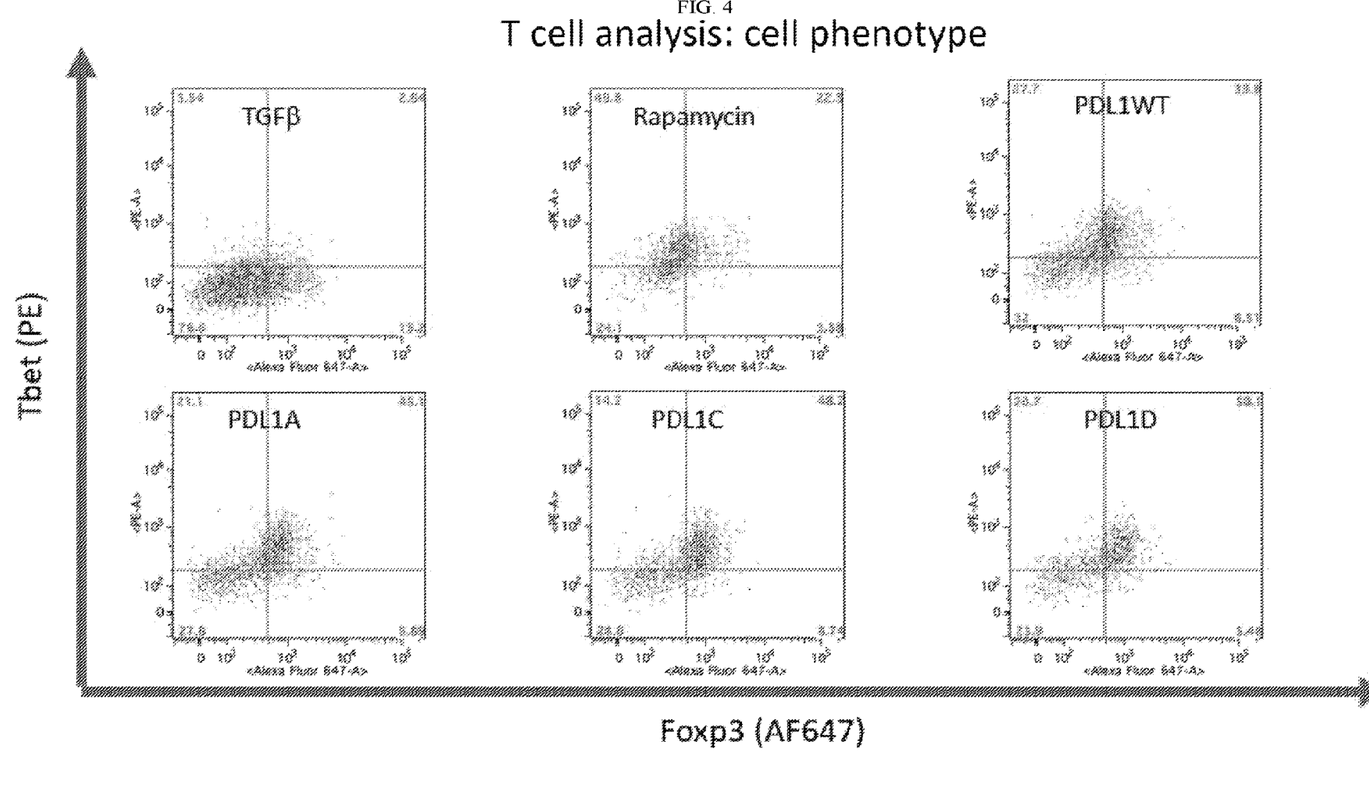
FIG. 4 shows the results of a flow cytometry analysis of Th1 cells treated with the mutant PD-L1 peptides as compared to cells treated with TGFβ or rapamycin (positive controls) or with the wild-type PD-L1 peptide (PDL1WT).

Day 1 T cells were cultured in X-Vivo™ media containing 5% AB serum, INF-γ, 20 U/ml IL-2, and CD3/CD28 coated beads to activate the cells into CD4+ effector T (Th1) cells. Two days later, the cells were analyzed by western blot and flow cytometry for expression of the Treg- and Th1-specific transcription factors, Foxp3 and Tbet, respectively. On day 6, the Th1 cells were seeded into 24-well plates with CD3/CD28 beads without IL-2, in the presence and absence of beads coated with mutant PD-L1 peptides. On day 8, cells were collected and analyzed via flow cytometry (see FIG. 2 for a schematic of this process) to determine the percentage of viable CD4+ cells (FIG. 3) and the percentage of cells with a Treg phenotype (FIG. 4).

Figure 5:
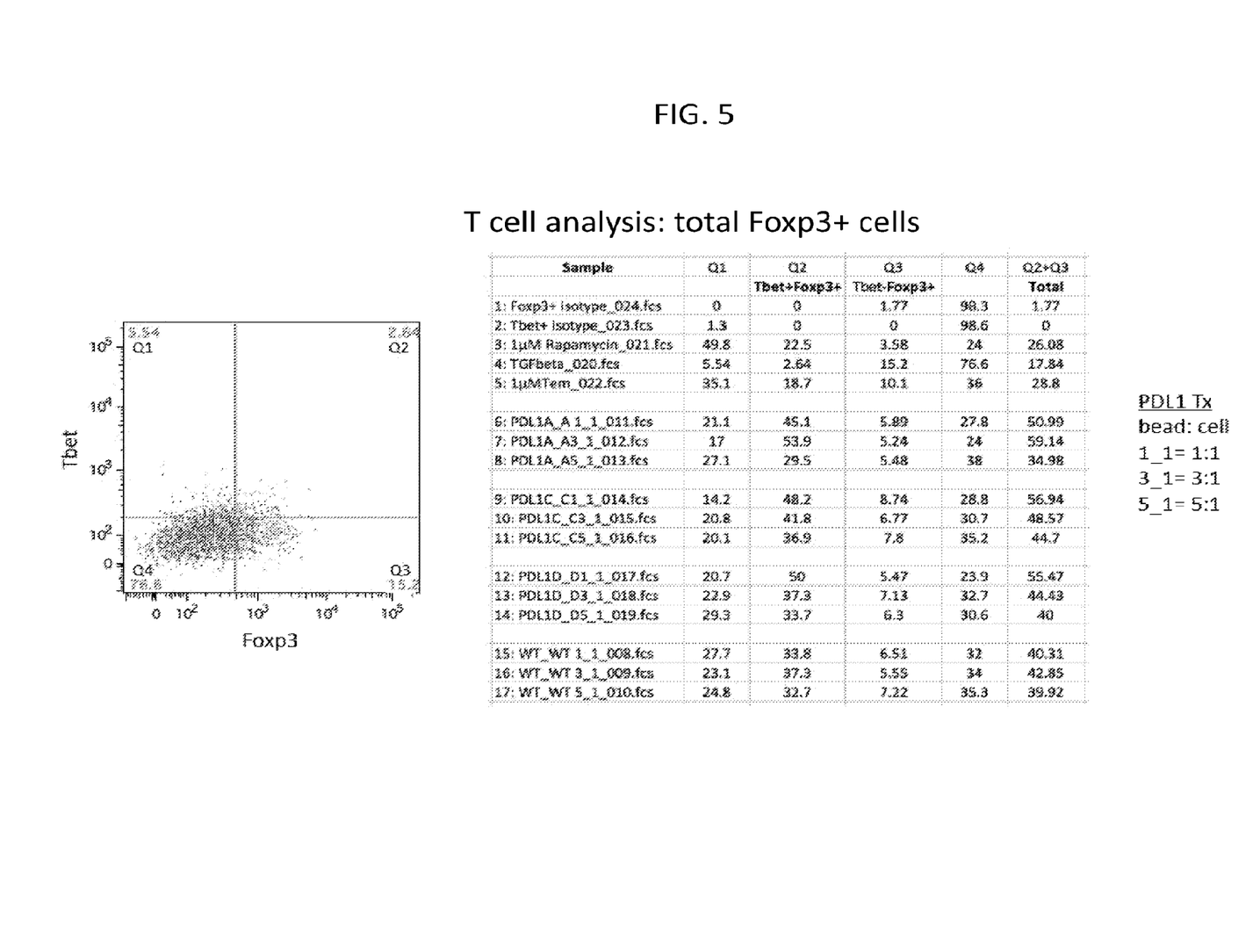
FIG. 5 shows the amount of Treg cells (Foxp3+) produced by treating T cells with the mutant PD-L 1 peptides (quadrant 2 and quadrant 3 cells) as compared to the wildtype PD-L 1 peptide (PDL1WT).

This analysis revealed that the expression of Foxp3 was significantly increased in cells incubated with PD-L1-coated beads as compared to control (e.g., increased compared to TGF-sample alone. TGF-β is normally used for expansion of Tregs (standard protocol)) while the expression of Tbet was significantly reduced (FIG. 4 and FIG. 5). The results demonstrate that the truncated PD-L1 constructs are able to direct Th1 cells to differentiate into Treg cells with greater efficiency than wild-type PD-L1 fragments.

Ongoing work will characterize the cellular changes produced by treatment with the PD-L1-coated beads (e.g., expression of extracellular markers, changes to intracellular signaling). Additionally, the efficacy of the differentiated Treg cells for the treatment of type I diabetes will be evaluated in vivo utilizing a mouse model.

The invention claimed is:

1. A soluble mutant programmed death-ligand 1(PD-L1) peptide consisting essentially of SEQ ID NO: 1, wherein the PD-L1 peptide comprises one or more mutations selected from the group consisting of D9E, D105E, Y106W, R108M, Y39I, S100I, V51I, and combinations thereof, and wherein the position of each mutation is numbered relative to SEQ ID NO: 1.

2. The soluble mutant PD-L1 peptide of claim 1, wherein the PD-L1 peptide comprises two or more mutations selected from the group consisting of D9E, D105E, Y106W, R108M, Y39I, S100I, V51I, and combinations thereof.

3. The soluble mutant PD-L1 peptide of claim 1, wherein the PD-L1 peptide comprises three or more mutations selected from the group consisting of D9E, D105E, Y106W, R108M, Y39I, S100I, and combinations thereof.

4. The soluble mutant PD-L1 peptide of claim 1, wherein the PD-L1 peptide comprises four or more mutations selected from the group consisting of D9E, D105E, Y106W, R108M, Y39I, S100I, V51I, and combinations thereof.

5. The soluble mutant PD-L1 peptide of claim 1, wherein the PD-L1 peptide comprises five or more mutations selected from the group consisting of D9E, D105E, Y106W, R108M, Y39I, S100I, V51I, and combinations thereof.

6. The soluble mutant PD-L1 peptide of claim 1, wherein the PD-L1 peptide comprises six or more mutations selected from the group consisting of D9E, D105E, Y106W, R108M, Y39I, S100I, V51I, and combinations thereof.

7. The soluble mutant PD-L1 peptide of claim 1, wherein the PD-L1 peptide comprises the following mutations: D9E, D105E, Y106W, R108M, Y39I, S100I, and V51I.

8. The soluble mutant PD-L1 peptide of claim 1, wherein the peptide consists essentially of an amino acid sequence selected from:

(a)
```
                                          (PDL1A; SEQ ID NO: 2)
AFTVTVPKDLYVVEYGSNMTIECKFPVEKQLDLAALIVYWEMEDKNIIQ
FVHGEEDLKVQHSSYRQRARLLKDQLSLGNAALQITDVKLQDAGVYRCM
ISYGGADWKRITVKVNAPY,
```

(b)
```
                                          (PDL1C; SEQ ID NO: 3)
AFTVTVPKDLYVVEYGSNMTIECKFPVEKQLDLAALIVIWEMEDKNIIQ
FIHGEEDLKVQHSSYRQRARLLKDQLSLGNAALQITDVKLQDAGVYRCM
IIYGGADWKRITVKVNAPY,
```
and (c)
```
                                          (PDL1D; SEQ ID NO: 4)
AFTVTVPKELYVVEYGSNMTIECKFPVEKQLDLAALIVIWEMEDKNIIQ
FIHGEEDLKVQHSSYRQRARLLKDQLSLGNAALQITDVKLQDAGVYRCM
IIYGGAEWKMITVKVNAPY.
```

9. The soluble mutant PD-L1 peptide of claim 1, wherein the peptide further comprises a tag or agent.

10. A polynucleotide encoding the soluble mutant PD-L1 peptide of claim 1.

11. A vector capable of expressing the soluble mutant PD-L1 peptide, the vector comprising a promoter operably connected to a polynucleotide encoding the soluble mutant PD-L1 peptide of claim 1.

12. The vector of claim 11, further comprising heterologous backbone sequence.

13. A host cell comprising the vector of claim 11.

14. A soluble mutant PD-L1 peptide-bead complex, the complex comprising the soluble mutant PD-L1 peptide of claim 1 and a bead, wherein the peptide is covalently or non-covalently attached to the bead.

15. A method of generating regulatory Foxp3+T cells (Foxp3+Tregs), the method comprising contacting T cells cultured in vitro with the soluble mutant PD-L1 peptide of claim 1 or the soluble mutant PD-L1 peptide-bead complex of claim 14 in an amount effective to generate Treg cells, wherein the soluble mutant PD-L1 peptide comprises SEQ ID NO: 2 (PDL1A), SEQ ID NO: 3 (PDL1C), or SEQ ID NO: 4 (PDL1D).

\* \* \* \* \*

UNITED STATES PATENT AND TRADEMARK OFFICE
CERTIFICATE OF CORRECTION

PATENT NO. : 12,006,511 B2
APPLICATION NO. : 17/046287
DATED : June 11, 2024
INVENTOR(S) : Kaothara Oluwakemi Adeyanju et al.

It is certified that error appears in the above-identified patent and that said Letters Patent is hereby corrected as shown below:

In the Specification

Column 4, Line 51, "S1171" should be --S117I--.

Column 4, Line 58, "S1171" should be --S117I--.

Column 4, Line 60, "S1171" should be --S117I--.

Column 5, Line 1, "S1171" should be --S117I--.

Column 12, Line 28, "TGF-sample" should be --TGF-β sample--.

In the Claims

Claim 1, Column 17, "S1001" should be --S100I--.

Claim 5, Column 17, "S1001" should be --S100I--.

Claim 6, Column 17, "S1001" should be --S100I--.

Signed and Sealed this
Twentieth Day of August, 2024

Katherine Kelly Vidal
*Director of the United States Patent and Trademark Office*